US010751689B2

(12) United States Patent
Goeppert et al.

(10) Patent No.: US 10,751,689 B2
(45) Date of Patent: Aug. 25, 2020

(54) REGENERATIVE ADSORBENTS OF MODIFIED AMINES ON SOLID SUPPORTS

(71) Applicant: UNIVERSITY OF SOUTHERN CALIFORNIA, Los Angeles, CA (US)

(72) Inventors: Alain Goeppert, Los Angeles, CA (US); Hang Zhang, Los Angeles, CA (US); George A. Olah, Los Angeles, CA (US); G. K. Surya Prakash, Los Angeles, CA (US)

(73) Assignee: UNIVERSITY OF SOUTHERN CALIFORNIA, Los Angeles, CA (US)

(*) Notice: Subject to any disclaimer, the term of this patent is extended or adjusted under 35 U.S.C. 154(b) by 369 days.

(21) Appl. No.: 14/991,886

(22) Filed: Jan. 8, 2016

(65) Prior Publication Data

US 2016/0199810 A1 Jul. 14, 2016

Related U.S. Application Data

(60) Provisional application No. 62/102,511, filed on Jan. 12, 2015.

(51) Int. Cl.
*B01J 20/26* (2006.01)
*B01J 20/10* (2006.01)
(Continued)

(52) U.S. Cl.
CPC ............ *B01J 20/103* (2013.01); *B01D 53/02* (2013.01); *B01D 53/04* (2013.01); *B01J 20/262* (2013.01); *B01J 20/28007* (2013.01); *B01J 20/3078* (2013.01); *B01J 20/3204* (2013.01); *B01J 20/3231* (2013.01); *B01J 20/3272* (2013.01); *B01J 20/3425* (2013.01); *B01J 20/3483* (2013.01); *B01J 20/3491* (2013.01); *C07C 29/48* (2013.01); *C07C 41/01* (2013.01); *C07C 51/16* (2013.01); *B01D 2253/202* (2013.01);
(Continued)

(58) Field of Classification Search
None
See application file for complete search history.

(56) References Cited

U.S. PATENT DOCUMENTS

| 4,044,100 A | 8/1977 | McElroy, Jr. |
| 4,112,185 A | 9/1978 | Meiller |

(Continued)

FOREIGN PATENT DOCUMENTS

| WO | 2004/054708 A2 | 7/2004 |
| WO | 2008/021700 A1 | 2/2008 |
| WO | 2010/091831 A1 | 8/2010 |

OTHER PUBLICATIONS

International Search Report and Written Opinion, PCT/US2016/012663, dated May 10, 2016.

(Continued)

*Primary Examiner* — Anita Nassiri-Motlagh
(74) *Attorney, Agent, or Firm* — Winston & Strawn LLP

(57) ABSTRACT

The invention relates to regenerative, solid sorbents for adsorbing carbon dioxide from a gas mixture, including air, with the sorbent including a modified polyamine and a solid support. The modified polyamine is the reaction product of an amine and an epoxide. The sorbent provides structural integrity, as well as high selectivity and increased capacity for efficiently capturing carbon dioxide from gas mixtures, including the air. The sorbent is regenerative, and can be used through multiple cycles of adsorption-desorption.

15 Claims, 3 Drawing Sheets

$RNH_2 + H_2C\overset{O}{-}CH\text{—}\diagdown\diagdown \longrightarrow RN(H)\text{—}CH_2\text{—}CH(OH)\text{—}\diagdown\diagdown$ Primary amine → Secundary amine $RN(H)\text{—}CH_2\text{—}CH(OH)\text{—}\diagdown\diagdown + H_2C\overset{O}{-}CH\text{—}\diagdown\diagdown \longrightarrow RN(CH_2CH(OH)\text{—}\diagdown\diagdown)_2$ Tertiary amine

(51) Int. Cl.
   *B01J 20/28*     (2006.01)
   *B01J 20/30*     (2006.01)
   *B01J 20/32*     (2006.01)
   *B01J 20/34*     (2006.01)
   *B01D 53/02*     (2006.01)
   *B01D 53/04*     (2006.01)
   *C07C 29/48*     (2006.01)
   *C07C 41/01*     (2006.01)
   *C07C 51/16*     (2006.01)

(52) U.S. Cl.
   CPC .... *B01D 2253/25* (2013.01); *B01D 2257/504* (2013.01); *Y02C 10/04* (2013.01); *Y02C 10/08* (2013.01)

(56) References Cited

U.S. PATENT DOCUMENTS

| | | |
|---|---|---|
| 4,810,266 A | 3/1989 | Zinnen et al. |
| 5,087,597 A | 2/1992 | Leal et al. |
| 5,376,614 A | 12/1994 | Birbara et al. |
| 5,492,683 A | 2/1996 | Birbara et al. |
| 5,876,488 A | 3/1999 | Birbara et al. |
| 6,364,938 B1 | 4/2002 | Birbara et al. |
| 6,547,854 B1 | 4/2003 | Gray et al. |
| 7,605,293 B2 | 10/2009 | Olah et al. |
| 7,795,175 B2 | 9/2010 | Olah et al. |
| 8,212,088 B2 | 7/2012 | Olah et al. |
| 8,440,729 B2 | 5/2013 | Olah et al. |
| 8,557,027 B2 | 10/2013 | Peiffer et al. |
| 2012/0160097 A1 | 6/2012 | Peiffer et al. |

OTHER PUBLICATIONS

Li et al., "Preparation and Adsorption Properties of Polyethylenimine Containing Fibrous Adsorbent for Carbon Dioxide capture," Journal of Applied Polymer Science, 108(6)3851-3858 (Jan. 2008).

Li et al., "CO2 Capture by Polyethylenimine-Modified Fibrous Adsorbent," Langmuir, 24(13):6567-6574 (Jul. 2008).

REGENERATIVE ADSORBENTS OF MODIFIED AMINES ON SOLID SUPPORTS

This application claims the benefit of U.S. provisional application 62/102,511 filed Jan. 12, 2015, the entire content of which is expressly incorporated herein by reference thereto.

GOVERNMENTAL SUPPORT AND INTEREST

This invention was made with government support under DE-AR0000136 awarded by the Department of Energy (Advanced Research Projects Agency-Energy). The government has certain rights in the invention.

FIELD OF THE INVENTION

The invention relates to regenerative adsorbents based on a modified polyamine and a solid support for capturing and separating carbon dioxide from gas mixtures, including the air.

BACKGROUND OF THE INVENTION

Climate change and global warming is considered one of today's the most pressing and severe environmental problems. It is now generally accepted that the main cause for global warming is the release of so-called greenhouse gases into the atmosphere. A major greenhouse gas is carbon dioxide ($CO_2$), which is released predominantly from combustion of fossil fuels such as coal, petroleum and natural gas. Together, these fossil fuels supply about 80% of the energy needs of humanity. Because fossil fuels are still relatively inexpensive and easy to use, and since no satisfactory alternatives are yet available to replace them on the enormous scale needed, they are expected to remain our main source of energy for the foreseeable future.

One way to mitigate $CO_2$ emissions and their influence on the global climate is to efficiently and economically capture $CO_2$ from its point sources, such as from the emissions of fossil fuel-burning power plants and various industrial factories, naturally occurring $CO_2$ accompanying natural gas, and the air, and then to sequester or convert the obtained $CO_2$ to renewable fuels and materials.

Among various $CO_2$ collection or separation techniques, amine solution-based $CO_2$ absorption/desorption systems are still one of the most suitable for capturing $CO_2$ from high volume gas streams. Commonly used solvents in such systems are aqueous solutions of alkanolamines such as monoethanolamine (MEA), diethanolamine (DEA), diisopropanolamine (DIPA), and methyldiethanolamine (MDEA). Certain sterically hindered amines, such as 2-amino-2-methyl-1-propanol (AMP), can also be used as absorbents because of their high $CO_2$ loading capacities. Of these, MEA is most widely used because of its high $CO_2$ absorption rate, which allows use of shorter absorption columns. The MEA system presents major drawbacks, however, including the large amount of heat required to regenerate the aqueous solution and operational problems caused by corrosion and chemical degradation. To prevent excessive corrosion, typically only 10 to 30 weight % MEA is used in an aqueous amine solution, with the rest being water. Because the entire solution, of which 70 to 90% is water, must be heated to regenerate the MEA system, a large amount of energy is wasted during the regeneration process. Other alkanolamine systems also present disadvantages. For example, secondary and hindered amines (e.g., DEA, DIPA, AMP) provide more moderate $CO_2$ absorption rates than MEA, and are also prone to corrosion and chemical degradation. MDEA is known to absorb $CO_2$ only at a slow rate. Formulations formed by blending several alkanolamines are of interest because they can combine favorable characteristics of various compounds while suppressing in part their unfavorable characteristics. A number of blended alkanolamine solutions have been developed, and the most common blends are MDEA-based solution containing MEA or DEA. However, blended alkanolamine solutions do not eliminate the drawbacks of amine solution-based systems.

$CO_2$ can also be captured by adsorption on solid sorbents. Solids are typically used as physical adsorbents for separation of $CO_2$. Such processes are based on the ability of porous solids to reversibly adsorb certain components in a mixture. The solids can have a large distribution of pore size, as in silica gel, alumina, and activated carbon, or a pore size controlled by the crystal structure, e.g., shape selective zeolites. At low temperatures such as room temperature, zeolite-based adsorbents have high $CO_2$ absorption capacities (e.g., 160 mg $CO_2$/g for zeolite 13X and 135 mg $CO_2$/g for zeolite 4A at 25° C. in pure $CO_2$). However, the adsorption capacities of these adsorbents decline rapidly with increasing temperature and in the presence of water or moisture. Further, because gases are only physically adsorbed on the adsorbents, actual separation of an individual gas from a mixture of gases is low.

To achieve a higher selectivity for $CO_2$ adsorption, a compound providing chemical absorption can be applied on the solid adsorbent. For this purpose, an amine or polyamine can be deposited or grafted onto a solid support. Amines and polyamines chemically bound (grafted) on the surface of solids, such as silicas and alumina-silicas, however, show in general limited adsorption capacity of less than 90 mg $CO_2$/g and, in most cases, less than 50-60 mg $CO_2$/g absorbent under dry conditions (Choi, S. et al., ChemSusChem, 2, 796-854, (2009)). For example, U.S. Pat. No. 5,087,597 to Leal et al. discloses a method for chemisorption of $CO_2$ at room temperature using silica gel having a surface area between 120 and 240 $m^2$/g, which is modified with a polyalkoxysilane containing one or more amino moieties in its structure. The material is disclosed to be capable of absorbing between 15 and 23 mg of dry $CO_2$ per gram of absorbent. U.S. Pat. No. 6,547,854 to Gray et al. discloses a method for preparing amine-enriched sorbents by incorporating the amine onto the surface of oxidized solids. The reported maximum amount of $CO_2$ absorbed on these solids is reported to be 7.7 mg/g absorbent using a gas mixture of 10% $CO_2$ in Helium. As is evident from the data, the amount of $CO_2$ that can be absorbed on the grafted amino group on various solid supports remains relatively low, because of their low amine coverage. Hyperbranched amino silica in which aziridine is polymerized directly off the surface of the silica offers somewhat higher amine content and higher $CO_2$ adsorption capacity (Hicks, J. C. et al., *J. Am. Chem. Soc.* 130: 2902, 2008).

Another pathway involves impregnating a solid support with amines or polyamines. For example, a paper by S. Satyapal et al., *J. Energy and Fuels* 15:250 (2001) describes the development of polyethylenimine (PEI)/polyethylene glycol (PEG) on a high surface area polymethylmethacrylate polymeric support. This solid was developed to be used in spacecrafts to remove $CO_2$ from the cabin atmosphere and release it into space. Its capacity is approximately 40 mg $CO_2$/g absorbent at 50° C. and 0.02 atm. $CO_2$. This material and its modifications are disclosed in U.S. Pat. Nos. 6,364,938; 5,876,488; 5,492,683; and 5,376,614 to Birbara et al.

The preferred supports described in these patents are of polymeric nature, with acrylic ester resins such as AMBERLITE® being described as having particularly suitable characteristics. U.S. Pat. Nos. 5,376,614; 5,492,683; and 5,876,488 also disclose other possible supports, including alumina, zeolite and carbon molecular sieves. According to U.S. Pat. Nos. 5,492,683 and 5,376,614, however, the amount of amine present on the sorbent is limited, ranging from 1 wt. % to 25 wt. %.

U.S. Pat. No. 4,810,266 to Zinnen et al. discloses a method for creating $CO_2$ sorbents by treating carbon molecular sieves with amine alcohols. This patent discloses that monoethanolamine (MEA)-based materials are not stable and release MEA during the regeneration step at higher temperatures. International Publication No. WO 2004/054708 discloses adsorbents based on mesoporous silica supports. The active components for $CO_2$ adsorption are amines or mixture thereof chemically connected or physically adsorbed on the surface of the mesoporous silicas. Adsorption on most of the adsorbents described in this publication is below 70 mg $CO_2$/g. The best results are obtained by using diethanolamine (DEA), which is physically adsorbed on the support (about 130 mg $CO_2$/g). However, because of the volatility of DEA under the desorption conditions, the effectiveness of this adsorbent generally decreases with increasing number of $CO_2$ adsorption-desorption cycle (a decrease of about 16.8% after 5 cycles at a moderate regeneration temperature of only 60° C.). U.S. Pat. No. 6,908,497 to Sirwardane et al. discloses a method for preparing sorbents by treating a clay substrate having a low surface area of 0.72 to 26 $m^2$/g with an amine and/or ether.

Alcohols, polyethylene glycol and other oxygenated compounds have also been used for decades for acid gas removal, mainly $CO_2$ and $H_2S$. For example, SELEXOL® from Union Carbide (now Dow Chemicals) and SEPASOLV MPE® from BASF are used in commercial processes. Oxygenated compounds in combination with amines as mixed physical or chemical sorbents, in a process such as a glycol-amine process, have also been used for many years for acid gas removal (see Kohl, A. L. and Nielsen, R. B., GAS PURIFICATION 5th ed. 1997, (Gulf Publishing Co.)). U.S. Pat. No. 4,044,100 to McElroy demonstrates the use of mixtures of diisopropanolamine and dialkyl ethers of a polyethylene glycol for removing gases, including $CO_2$ from gaseous streams. The use of ethylene glycol to improve the absorption and desorption of $CO_2$ from amines has also been studied by J. Yeh et al., *Energy and Fuels* 15, pp. 274-78 (2001). While the literature mainly relates to the use of amines and oxygenated compounds in the liquid phase, the use of oxygenated compounds to improve characteristics of gas sorbents in the solid phase has also been explored. S. Satyapal et al., *Energy and Fuels* 15:250 (2001) mentions the use of polyethylene glycol in conjunction with polyethyleneimine on a polymeric support to remove $CO_2$ from the closed atmosphere of a space shuttle. X. Xu et al., *Microporous and Mesoporous Materials* 62:29 (2003) shows that polyethylene glycol incorporated in a mesoporous MCM-41/polyethyleneimine sorbent improves the $CO_2$ adsorption and desorption characteristics of the tested material. Preparation and performance of a solid adsorbent consisting of PEI deposited on a mesoporous MCM-41 is also disclosed (see X. Xu et al., *Energy and Fuels* 16:1463 (2002)). U.S. Pat. Nos. 5,376,614 and 5,492,683 to Birbara et al. use polyols to improve adsorption and desorption qualities of the adsorbents. Improvements were also noticed by Goeppert et al. (Energ. Environ. Sci. 3:1949-1960, (2010)) and Meth et al. (Energ. Fuel. 26: 3082-3090(2012)).

Another new material for trapping carbon dioxide are metal organic framework compounds. A preferred compound known as MOF-177 (J. Am. Chem. Soc., 2005, 127, 17998) has a room temperature carbon dioxide capacity of 140 weight percent at a relatively high pressure of 30 bar.

Yet another adsorbent for this purpose is a supported amine sorbent comprising an amine or an amine/polyol composition deposited on a nano-structured support, which provide structural integrity and increased $CO_2$ adsorption capacity. This material is disclosed in U.S. Pat. No. 7,795,175. The support for the amine and amine/polyol compositions is composed of a nano-structured solid. The nano-structured support can have a primary particle size less than about 100 nm, and can be nanosilica, fumed or precipitated oxide, calcium silicate, carbon nanotube, or a mixture thereof. The amine can be a primary, secondary, or tertiary amine or alkanolamine, aromatic amine, mixed amines or combinations thereof. In an example, the amine is present in an amount of about 25% to 75% by weight of the sorbent. The polyol can be selected from, for example, glycerol, oligomers of ethylene glycol, polyethylene glycol, polyethylene oxides, and ethers, modifications and mixtures thereof, and can be provided in an amount up to about 25% by weight of the sorbent.

Despite these prior disclosures, there still remains a need for an improved sorbent for capturing $CO_2$, which is efficient, economical, readily available and regenerative, and which provides a high removal capacity at ambient as well as elevated temperatures.

Instead of adding polyols and amines based sorbents to enhance the $CO_2$ adsorption/desorption properties, the alcohol groups could be chemically bound to the amines and polyamines. One of the possibilities is to react epoxides with the amino groups of these amines and polyamines. In fact this reaction is commonly used in many applications for the curing of so-called "epoxy resins" where an epoxy resin is reacted with an amino compound (epoxy hardener or curing agent). The two components are generally mixed just before use. Application are numerous and include the formation of adhesives, primers for paints, coatings, production of molds, laminates, castings, fixtures and others. Each primary amino group is theoretically capable of reacting with two epoxide groups, and each secondary amine group is capable of reacting with one epoxide group. The reaction of a primary amine with an epoxide leads to a secondary amine which can itself react further with an additional epoxide to form a tertiary amine, as shown in FIG. 1.

To obtain optimum properties in the product, the curing agent (amine) and epoxide are generally reacted in stoechiometric quantities. To be more precise, the amount of amine N—H bonds is chosen to be equivalent or close to the amount of epoxide groups in the epoxy resin, so that all the amine N—H bonds and epoxide groups would react to form a solid.

The formation of a solid where all the amine N—H bonds would have reacted to form mostly tertiary amines would not result in the most efficient $CO_2$ adsorption characteristics. Thus, these prior art material do not disclose or inherently provide desirable $CO_2$ adsorption.

The reaction of an amine with an epoxide increases the molecular weight of the obtained compounds resulting in a lower volatility. This is particularly important for relatively low molecular weight amines such as for example diethylenetriamine (DETA) triethylenetetramine, (TETA) and tetraethylenepentaamine (TEPA) which have a tendency to leach out when impregnated on solid support as was shown in a number of papers (Qi, G. et al. *Energy Environ. Sci.* 2012, 5, 7368; Liu, S.-H. et al. *Adsorption* 2012, 18, 431.; Yan, W. et al. *Ind. Eng. Chem. Res.* 2012, 51, 3653.; Wang, W. et al. *Energy & Fuels* 2013, 27, 1538; Qi, G. G. et al. *Energy Environ. Sci.* 2011, 4, 444.). When epoxides containing several epoxide groups (2, 3 or more) are used, crosslinking can occur between amines.

The crosslinking of amines with epoxides for the purpose of capturing $CO_2$ has been described to some extent. Andreopoulos et al. (*Polymers Advanced. Technol.* 1991, 2, 87-91) describes the impregnation of polyethylene fibers with polyethylenimine (PEI, Mw-50000-60000)/epoxy resin (Epon 828). The $CO_2$ adsorption capacity obtained was, however, very low, most likely due to the poor surface area of the support. There is no mention of recyclability of the adsorbent. The solvents used for the preparation of the adsorbents were methanol, acetone and dimethylformamide (DMF) which are not benign.

Li et al. (*J. Appl. Polym. Sci.* 2008, 108, 3851) coated PEI (Mw~25000)/epoxy resin (Bisphenol A epoxy resin) on a glass fiber matrix and obtained higher $CO_2$ adsorption capacities than the ones reported by Andreopoulos et al. The presence of moisture had a significant positive effect on the adsorption capacity. The solvents used for the preparation for the adsorbent were methanol and DMF.

Gebald et al. (WO 2010/091831 A1) also described the preparation of adsorbents based on fibrous materials on which crosslinked amine was impregnated. The crosslinked amine was the result of the reaction of an amine with an epoxy resin. The authors only described the reaction of two types of amines, i.e. PEI and TEPA, and one type of epoxy resin, i.e. D.E.R. 332, a bisphenol A diglycidylether manufactured by Dow Chemicals. The solvent used for the preparation of the adsorbent was ethanol.

A sorbent based on PEI and D.E.R. 332 on carbon fiber lead to an adsorption capacity of 56.8 mg $CO_2$/g adsorbent from a gas mixture containing 500 ppm $CO_2$ and 100% humidity at 20° C. At 50% relative humidity a much lower adsorption capacity of only 12.5 mg $CO_2$/g was obtained. Reacting TEPA with D.E.R. 332 gave an adsorbent with an adsorption capacity of 82.5 mg $CO_2$/g with a 50% relative humidity at 20° C. The PEI based adsorbent was tested for recyclability in three consecutive adsorption/desorption cycles during which, the adsorption capacity remained similar. On the other hand the adsorbent based on TEPA was not submitted to a similar treatment and recyclability was therefore not demonstrated. In the example for the preparation of TEPA/epoxy resin containing sorbent, the amount of epoxy resin was 0.55 g or 0.00161 mol. The amount of TEPA used was 5 g or 0.02641 mol. Even taking into account that the epoxy resin (D.E.R. 332) has two epoxide groups in each molecule able to react with amino groups, the molar ratio of TEPA/epoxide groups is still only 8.2 (amino groups/epoxide groups ratio of 41). Ideally a ratio of 1 or lower would be necessary for all TEPA molecules to react with at least one epoxide group. This means that due to this high ratio, a majority of the TEPA added at the beginning of the reaction is probably still present, unreacted, in the adsorbent material. The volatility problem of TEPA and other low molecular weight amines have been presented vide supra. It is therefore likely that the adsorbent based on TEPA described in this patent suffers from some leaching problems. Interestingly, the weight of the TEPA based adsorbent during TGA analysis dropped by only 28.5% when heated up to 750° C., which was significantly lower than the 50% expected, indicating some possible loss of TEPA during the preparation itself.

Peiffer et al. (U.S. Pat. No. 8,557,027) described the preparation of epoxy- amine materials for the purpose of $CO_2$ adsorption. The obtained materials were, however, not impregnated or deposited on any support. Their adsorption capacity seemed therefore quite limited at ambient to moderate temperatures (25-50° C.) and they exhibited their highest, although still limited, adsorption capacity at around 80-110° C. This implies that the $CO_2$ desorption would require even higher temperatures and/or a combination with lower pressure, meaning a higher energy input during the desorption. Furthermore, when porogens were used during the preparation to increase the surface area, an additional step of extraction of these porogens with solvents was required at the end of the synthesis.

Meiller (U.S. Pat. No. 4,112,185) described the preparation of an ion exchange resin based on modified porous materials with their surface covered with a cross-linking polymer resulting from the reaction of a polyamine with an epoxide. However, the epoxide compound was generally added in excess (by weight) compared to the amine compound, leading most probably to the formation of a large proportion of tertiary amines. While this resulted in materials with suitable properties for ion exchange application they would have had limited activity for $CO_2$ capture.

Considering the state of the art described here, improvements to the prior art materials is therefore now needed. The present invention now addresses the deficiencies of the prior art to provide new materials as well as their preparation on suitable supports for use in $CO_2$ adsorption.

SUMMARY OF THE INVENTION

The invention provides a new solid sorbent for adsorbing carbon dioxide from a gas mixture, comprising a modified polyamine and a solid support. As disclosed herein, the modified polyamine is the reaction product of an amine and an epoxide.

The support can be any suitable solid support, which after combination with the modified amine will result in the formation of a solid adsorbent.

A particularly suitable support is a so-called nano-structured solid support. A preferred nano-structured support advantageously has a primary particle size less than about 100 nm and preferably a size between 3 and 50 nm, 3 and 30 nm or 3 and 15 nm. The support is typically silica, silica-alumina, calcium silicate, carbon nanotube, or a mixture thereof. The support can also include various forms of suitable natural and synthetic clays (e.g. montmorillonite).

The addition of hydroxyl groups to amines has several benefits. As discussed in the "background of the invention", the addition of polyols has been shown to improve the reaction kinetics for the adsorption and desorption of $CO_2$ on amine based sorbents.

In the present invention, the amount of epoxide would typically be chosen such as at least one epoxide group reacts with at least one amino group in the amine molecule. For example in the case of TEPA (containing 5 amino groups) and a molecule with a single epoxide group such as propylene oxide (PO), a molar ratio of PO/TEPA of 1 or higher would be preferable. However, the number of epoxide groups should not be too high to avoid complete reaction of all the N—H bonds in the amino groups and subsequent poor $CO_2$ adsorption characteristics. The reaction of molecules with a single epoxide reactive group with amines allows an increase in the molecular weight of these amines, leading to lower volatility, higher stability and better adsorption/desorption characteristics.

If crosslinking is desired with an epoxy resin containing 2, 3 or more epoxide groups, the ratio between epoxide groups and amine should, ideally, be a least 1 to allow each amine molecule to react, theoretically, with a least one epoxide group. For example in the case of TEPA (containing 5 amino groups) and a molecule containing two epoxide units such as glycerol diglycidyl ether (GDGE), a molar ratio of GDGE/TEPA of a 0.5 or higher would be preferable. Addition of larger amounts of epoxide would allow for a higher degree of crosslinking resulting in higher molecular weight species which would further decrease the volatility of the amines.

The amount of epoxide to add will, however, also depend on the nature of the amine. For relatively low molecular weight amines such as diethylenetriamine (DETA) triethylenetetramine, (TETA), tetraethylenepentaamine (TEPA), pentaethylenhexamine (PEHA) the addition of epoxides will have a direct effect on their volatility by increasing their molecular weight through either addition of single epoxides or crosslinking with polyepoxides (2 or more epoxide groups in the same molecule). In the case of higher molecular weight amines such as polyethylenimine, which do not suffer to the same extent from the problem of volatility, the reaction with epoxides will also increase the molecular weight of the amines. Crosslinking could also further improve the stability of these amines. However, with higher molecular weight amines the benefits or the reaction with epoxide might reside more in the improved adsorption/desorption characteristics compared to the unmodified amine.

Any possible combination of amines and epoxides is of course possible to obtain the desired characteristics for a specific application. It is preferable to have an excess of amine compared to the amount of epoxide groups to provide materials with optimum $CO_2$ absorbing properties.

In another embodiment, the sorbent further comprises a polyol in an amount of 1% up to about 25% by weight of the sorbent. Typically, the polyol is selected from the group consisting of glycerol, oligomers of ethylene glycol, polyethylene glycol, polyethylene oxides, and ethers, modifications and mixtures thereof. In particular, when the nano-structured support is nanosilica, the modified amine may be present in an amount of about 1% to 90% by weight of the sorbent, and the sorbent further comprises polyethylene glycol in an amount of 1% up to 25% by weight of the sorbent.

The invention also relates to a method for preparing these sorbents, by combining the amine, epoxide and support in a solvent with mixing and heating for a sufficient time to allow the amine and epoxide to combine and be provided upon the support, followed by removal of the water to obtain the sorbent as a solid.

DETAILED DESCRIPTION OF THE INVENTION

Figure 1:
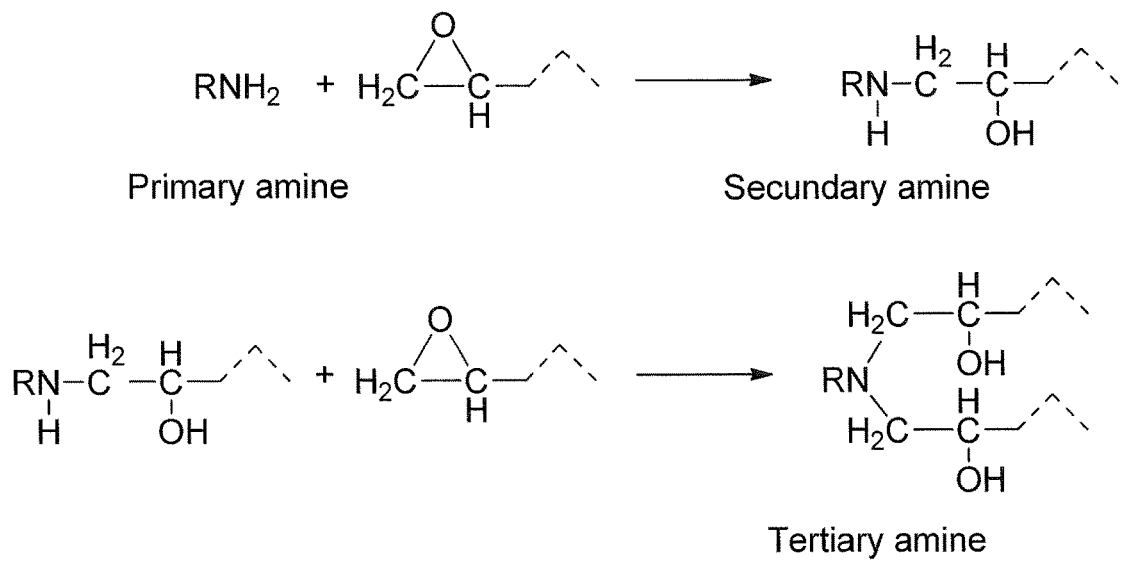
FIG. 1 illustrates the reaction of amines with epoxy resins

The invention relates to regenerative supported modified polyamine sorbents for absorbing $CO_2$. The sorbent comprises a modified polyamine on a nano-structured support, e.g., a nanosilica support, for adsorbing and desorbing $CO_2$. Carbon dioxide can be adsorbed from any desired source, including industrial exhausts, flue gases of fossil fuel-burning power plants, as well as natural sources such as ambient air. The nano-structured support according to the invention provides structural integrity to the polyamine as well as a high surface area for solid-gas contact. The support can also include natural and synthetic clays.

The modified polyamine sorbent with nano-scale support according to the invention provides significant advantages over the absorbents of the prior art, e.g., adsorbents having a polymeric support, including a high $CO_2$-selectivity and removal capacity at ambient and elevated temperatures. Thus, the present sorbent allows selective capture and separation of $CO_2$ from various gas mixtures under various conditions and temperatures.

The present sorbent is also easy to regenerate and recycle at ambient to moderate temperatures, enabling multiple adsorption-desorption cycles with no or minimal loss of activity. The sorbent also addresses the corrosion and evaporation problems of the prior art adsorbents.

Thus, the present sorbent system is practical for separating $CO_2$ from industrial effluent gases such as those from fossil fuel-burning power plants and other industrial factories, as well as other gas streams, particularly natural gas containing significant $CO_2$ concentrations. Significantly, the sorbent can also be used to separate $CO_2$ from atmospheric air.

The sorbent according to the invention is suggested to adsorb $CO_2$ by the following mechanism. Upon contact with a gaseous stream containing $CO_2$, the supported modified amine chemically adsorbs $CO_2$ by forming a carbamate complex.

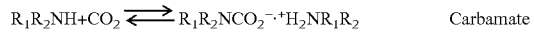
                                                               Carbamate In the presence of water, the carbamate further reacts to form a bicarbonate and releases the amine, which can further react with $CO_2$, thereby increasing the overall $CO_2$ adsorption capacity.

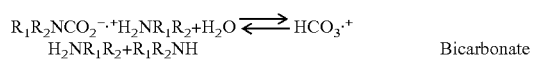
                                                               Bicarbonate According to an embodiment of the invention, the adsorbed $CO_2$ can be readily desorbed and the supported modified polyamine can be regenerated. The desorption of $CO_2$ and regeneration of the sorbent can be achieved by modest heating of the sorbent, applying reduced pressure or vacuum, gas purge, and/or a carbon dioxide lean sweep gas, which releases $CO_2$ from the sorbent. The ready regeneration enables the sorbent to undergo repeated absorption-desorption cycles with ease.

A large variety of amines can be used in the present invention. Suitable amines include primary, secondary and tertiary alkyl- and alkanolamines, aromatics, mixed amines, and combinations thereof. Polyamines are preferred. Primary and secondary amines are the most active for $CO_2$ absorption. The polyamine should, therefore, preferably contain a sufficient amount of primary and secondary amine sites. Specific examples of amines include, but are not limited to, tetraethylenepentaamine, pentaethylenehexamine, triethylenetetramine, diethylenetriamine, ethylenediamine, hexaethyleneheptamine, polyethylenimines, polyallylamines, polyvinylamines and the like, including various polymeric amine compounds and mixtures thereof.

Preferred polyamines include various higher ethyleneamines which are sometimes referred to as polyethyleneamines. A general formula for such polyamines is: $H(NH(CH_2)_n)_p NH_2$ where n is 1 to 4 and p is 2 to about 10,000. The polyamine preferably contains a sufficient amount of repeating $NH(CH_2CH_2)$ or $NH(CH_2)$ units so that they possess relatively low volatility to avoid or minimize loss of amine, which would contaminate the gas stream and decrease the effectiveness of the adsorption system over time. Specifically preferred linear polyamines include triethylenetetramine, (TETA), tetraethylenepentamine (TEPA), pentaethylenehexamine (PEHA) and hexaethyleneheptamine (HEHA).

Epoxides that can be used in this invention to modify the amine include single epoxides, as well as diepoxides, triepoxides and higher homologues. Examples of epoxide components include, but are not limited to, ethylene oxide, propylene oxide, 1,2-epoxybutane, 2,3-epoxybutane, glycidol, butyl glycidyl ether, tert-butyl glycidyl ether, dodecyl and tetradecyl glycidyl ethers, octyl/decyl glycidyl ether, 1,2-epoxycyclohexane, epichlorohydrin, glycerol diglycidyl ether, 1,4-cyclohexanedimethanol diglycidyl ether, neopentyl glycol diglycidyl ether, poly(ethylene glycol) diglycidyl ether, resorcinol diglycidyl ether, poly(propylene glycol) diglycidyl ether, 4,4'-isopropylidenediphenol diglycidyl ether, 1,2,5,6-diepoxycyclooctane, trimethylolpropane triglycidyl ether, N,N-diglycidyl-4-glycidyloxyaniline, 4,4'-methylenebis(N,N-diglycidylaniline) and the like, including mixtures thereof.

The support according to the invention is a support having primary particle sizes less than 1,000 nm, preferably less than about 100 nm. Preferred supports are nanosilica, especially so-called fumed silica and precipitated silica. Fumed silica typically has a primary particle size ranging from 5 to 50 nm and a specific surface area between 50 and 500 m²/g. Fumed silica is generally prepared by vapor phase hydrolysis of a silicon-bearing halide, such as silicon tetrachloride ($SiCl_4$). Examples of commercially available fumed silica include AEROSIL® from Evonik, CAB-O-SIL® from Cabot, and REOLOSIL® from Tokuyama. Precipitated silica is formed from aqueous solutions by reaction of an alkaline silicate (e.g., sodium silicate) with a mineral acid (e.g., sulfuric acid) under stirring. Primary particles formed by this method are generally between 3 and 50 nm, more specifically between 3 and 30 nm and preferably are between 3 and 15 nm in size. These primary particles can subsequently aggregate to form larger micron size particles. The specific surface area of precipitated silica generally ranges from 50 to 500 m²/g. Examples of commercially available precipitated silica include HI-SIL® from PPG Industries, SIPERNAT® from Evonik and FINESIL® and TOKUSIL® from Tokuyama.

Fumed silica and precipitated silica have the appearance of a lightweight, fluffy, white powder. Their small particle size allows them to absorb and retain significant amounts of amines while maintaining free flowing powder characteristics without caking. Another advantage of fumed and precipitated silicas is their non-toxicity. The non-toxicity allows them to be used in food processing, e.g., as anti-caking additives in powdered food products such as milk substitutes, and in cosmetic products, e.g., in abrasive material in a toothpaste. Fumed and precipitated silicas are generally hydrophilic, but their surface can be treated to produce hydrophobic silicas. Both hydrophilic and hydrophobic silicas, as well as other modified silicas, are all suitable for use as the nano-structured polyamine support according to the invention.

Other nano-structured materials suitable for use in the present polyamine sorbents include fumed or precipitated oxides such as fumed aluminum oxide, fumed zirconium oxide, and fumed titanium oxide, precipitated aluminum oxide, precipitated titanium oxide, precipitated zirconium oxide, calcium silicate, carbon nanotubes, and mixtures thereof. Other supports can also include natural and synthetic clays.

The supported polyamine sorbent can be prepared by impregnation or by another conventional technique.

To enhance the $CO_2$ adsorption and desorption characteristics of the supported amine sorbent, polyols may be incorporated in the sorbent composition, in an amount up to 25% of the total weight of the sorbent. The addition of polyols improves the adsorption and desorption of the sorbent, and decreases the viscosity of the amines, allowing $CO_2$ to have better access to the active amino sites of the sorbent even at lower temperatures (<50° C.). Polyols used in the invention should have low volatility to avoid or minimize material loss, which could contaminate the gas stream and decreases the effectiveness of the adsorption system over time. Examples of polyols used in the present sorbent include but are not limited to glycerol, oligomers of ethylene glycol, polyethylene glycols, polyethylene oxides, ethers of oligomers of ethylene glycol, ethers of polyethylene glycols, ethers of polyethylene oxides, oligomers or polymers of cyclic ethers such as polytetrahydrofuran, and modifications and mixtures thereof. Preferred polyols have a molecular weight lower than 10,000. More preferably, polyols have a molecular weight lower than 1,000.

The modified polyamine is obtained by dissolving the amine in a solvent, preferably water, to form an amine solution; adding the epoxide to the amine solution with agitation or stirring to form a mixture for a period of time and form a liquid reaction product of the amine and epoxide; and then heating the mixture, if needed, to ensure complete reaction, followed by heating, if necessary under vacuum conditions, to remove the solvent. The amine is a primary, secondary or tertiary alkyl- or alkanolamine, an aromatic amine, a mixed amine, or a combination thereof, while the epoxide is a simple epoxide, diepoxide, triepoxide, a polyepoxide compound, polymeric epoxide or a mixture thereof. A preferred polyamine is tetraethylenepentamine, pentaethylenehexamine, triethylenetetramine, diethylenetriamine, ethylenediamine, hexaethyleneheptamine, a polyethylenimine, or a combination thereof, while a preferred epoxide is ethylene oxide, propylene oxide, 1,2-epoxybutane, 2,3-epoxybutane, glycidol, butyl glycidyl ether, tert-butyl glycidyl ether, dodecyl and tetradecyl glycidyl ethers, octyl/decyl glycidyl ether, epichlorohydrin, glycerol diglycidyl ether, poly(ethylene glycol) diglycidyl ether, 4,4'-isopropylidenediphenol diglycidyl ether, trimethylolpropane triglycidyl ether or a mixture thereof. In the sorbent the modified polyamine is present in an amount of about 1% to 90% by weight or 40% to 70% by weight or in an approximately equal amount by weight of the support.

In one embodiment of the method of preparation, wherein the nano-structured support is dispersed in the solvent to form a suspension; the amine is dissolved in the solvent to form an amine solution; the epoxide is dissolved in a solvent to form an epoxide solution; and the suspension and the amine and epoxide solutions are combined. This can be conducted by dissolving the amine in solvent to form an amine solution, adding this solution to the support suspension, and then adding the epoxide solution to the amine/support mixture; mixing the mixture at a temperature of 15 to 30° C. for 0.1 to 50 hours; then heating the mixture to ensure complete reaction, and finally heating to at least 50° C. for 30 seconds to 60 minutes to remove part or all of the solvent, with any remaining solvent removed by heating if necessary under vacuum.

Alternatively, the amine and epoxide can be reacted separately to obtain a modified amine after removal of the solvent. The sorbent is formed by adding the modified amine to the dispersion of the support in solvent with stirring to disperse the modified polyamine onto the support. Alternatively, the reaction product of amine and epoxide can be added directly to the support suspension, without prior solvent removal.

If the epoxide is a liquid it can also be added neat without the need of dissolving it in a solvent.

In another embodiment, the method of preparation further comprises adding a polyol before the removing solvent for the obtention of the sorbent. In particular, the method further comprises adding a polyol to the suspension; drying the suspension after the addition of the polyol to form a supported polyol; dispersing the supported polyol in the solvent; and combining the dispersed supported polyol and the amine solution prior to removing the solvent to obtain the sorbent.

Because it is environmentally benign and very economic, the preferred solvent is water. Water is able to form solution with most amines described here as well as a number of epoxides including but not limited to propyleneoxide, 1,2-epoxybutane, glycidol, glycerol diglycidyl ether, poly(ethylene glycol) diglycidyl ether. However, in some cases the use of other solvents including but not limited to methanol, ethanol and isopropanol might be necessary.

To enhance the stability of the modified amines further, chemical bonding of these modified amines to surface of the supports by any known method including grafting with various species is also possible.

The amine-epoxide based $CO_2$ adsorbents described here are efficient, regenerable under mild conditions, easy to prepare from readily available starting materials, economical and have high $CO_2$ adsorption capacity. As such they fill most if not all of the desirable characteristics for a $CO_2$ adsorbent for post combustion $CO_2$ capture and $CO_2$ capture from various dilute sources such as ambient air which include:

Fast adsorption of $CO_2$ at mild temperatures or room temperature
Able to work under humid conditions
Fast desorption under mild conditions
No leaching of the active part
Long term stability under working conditions
Low cost
Easy to produce on a large scale The invention also relates to a method of capturing and separating carbon dioxide from a gas source by adsorbing the carbon dioxide on the sorbent. The sorbent is regenerative in that it can be desorbed and regenerated by applying heat, reduced pressure, vacuum, gas purge, lean sweep gas, or a combination thereof. In this regard, the invention also relates to the use of a modified polyamine to provide a solid sorbent for adsorbing carbon dioxide from a gas mixture, characterized in that the modified polyamine is the reaction product of an amine and an epoxide and is provided upon a nano-structured solid support.

The released carbon dioxide can be used in a method to produce a renewable fuel such as methanol. In one embodiment, this method comprises reduction of carbon dioxide and water, or reduction of carbon dioxide under conditions sufficient to produce methyl formate as an intermediate compound followed by catalytic hydrogenation of the intermediate compound with hydrogen to form methanol.

In another embodiment, methanol is produced by catalytic hydrogenation of the intermediate compound wherein the hydrogen used in the hydrogenation is obtained by electrolysis of water obtained from the air. In another embodiment, methanol is produced by reducing the carbon dioxide under conditions sufficient to carbon monoxide, reacting the carbon monoxide with methanol under conditions sufficient to obtain methyl formate, and catalytically hydrogenating the methyl formate under conditions sufficient to produce methanol.

Methanol produced according to the invention can be further processed to any desired derivative or modified compounds. For example, methanol can be dehydrated to produce dimethyl ether, which can also be further treated under conditions sufficient to form compounds such as ethylene and propylene. Ethylene and propylene can be converted to higher olefins, a synthetic hydrocarbons, aromatics, or related products, and therefore are useful as a feedstock for chemicals or as transportation fuel. In a further embodiment, methanol can be further used for microbiological production of single cell proteins.

The methods for preparing polyamine supported sorbents according to the invention are inexpensive and easy to carry out, yet produce sorbents that are superior to the sorbents prepared by previously known methods.

For example, the modified polyamine can be prepared by first dissolving the amine in water to form an amine solution. Next, an aqueous solution of epoxide is added to the amine solution to form a mixture. The mixture is initially stirred at room temperature (i.e., 15 to 30° C.) for 0.01 to 50 hours and preferably 0.01 to 10 hours and then is heated for 30 seconds to 1000 minutes and preferably from 10 to 300 minutes to allow the reaction to run to completion and then heated to a higher temperature to remove part or all of the water. Any remaining water can be removed by heating under vacuum. The obtained modified amine is generally a viscous liquid.

To form the sorbent, the obtained modified amine can be dissolved in water and added to the support (e.g., silica) in suspension in water with stirring to disperse the modified polyamine onto the support. The amount of modified amine would be between 1 and 90% or between 40 and 70% of the combined weight of the modified amine and support or in approximately equal amount by weights with the support. Thereafter, the water can be removed as described above.

The supported modified polyamine sorbent can be obtained as a solid, which could be crushed and sieved to produce a solid with a uniform size particle distribution for use in the adsorption of carbon dioxide.

Alternatively, the modified amine and sorbent can be prepared together by mixing the amine and silica into water as noted above, followed by the addition of a solution of the epoxide. Stirring or agitation of the mixture is maintained to form the sorbent and then the water is removed to obtain the sorbent as a solid.

Alternatively, the reaction product of amine and epoxide can be added directly to the support suspension, without prior water removal.

If the epoxide is a liquid it can also be added neat to the reaction mixture without the need of dissolving it first in a solvent.

As noted above, polyols can be added to enhance the adsorption/desorption characteristics of the supported amine sorbent. When a polyol is used, the polyol can be mixed together with the modified amine solution and added to the suspension of the support. The polyol can also be separately dissolved in the solvent and combined with the suspension of the support. In that case, the polyol solution is preferably added first to the suspension of the support, and the solvent is then removed to obtain the supported polyol material. The obtained solid is then dispersed in the solvent and a solution of the modified amine in the solvent is added under stirring. Finally, solvent is removed to form the supported modified amine/polyol sorbent. The sorbent can be used as is or can be crushed and sieved to obtain a solid with a uniform particle size distribution. It can also be crushed to a powder. The formation of the modified amine by reaction of an amine and an epoxide can also be conducted in-situ in the presence of the polyol.

Any solvent which is capable of dissolving, but which does not react, at least rapidly, with the amine, the epoxide and the polyol can be utilized. The solvent should preferably be easily separated from the sorbent by mild heating and/or vacuum. Preferred solvents include but are not limited to water and alcohols, which can dissolve amines, epoxides and polyols and can be easily removed from the sorbent. For example, water, methanol, ethanol, and isopropyl alcohol, and various mixtures thereof can be used.

Advantageously, the invention enables a wide range of $CO_2$ adsorbing capabilities for use with various natural and industrial gas sources. The adsorption can be performed under various conditions, e.g., over a temperature range of 0 to 100° C., and in any suitable manner, e.g., in a regular flow system or in a fixed, moving, or fluidized adsorption bed. The ability of the sorbent to capture $CO_2$ can be demonstrated by measuring adsorption by thermogravimetry using a thermogravimetric analyzer (TGA), in a flow system over a sorbent cartridge or by measuring $CO_2$ absorption under static conditions.

Once the amine containing sorbent is saturated with $CO_2$, the sorbent can be regenerated. As used herein, the term "regeneration" or "regenerative" is understood to mean that the sorbent can be re-used by releasing or desorbing the adsorbed gas from the sorbent. The adsorbed gas is released by treating the sorbent with any process that effects the release, e.g., heating, reduced pressure, vacuum, gas purge, and combinations thereof. Thus, the regenerated sorbent according to the invention can be used repeatedly, through multiple adsorption-desorption cycles. In an example, the sorbent maintains its adsorption efficiency even after repeated absorption-desorption cycles. Preferably, the sorbent maintains its absorption efficiency for many adsorption-desorption cycles. It is convenient to use parallel adsorption units, which allow adsorption and desorption/regeneration to be carried out continuously.

For example, for a $CO_2$ sorbent, the regeneration is endothermic, so the absorbed $CO_2$ is released by subjecting the absorbent to elevated temperature (e.g., by heating the sorbent at temperatures from about 25° C. to about 120° C.), reduced pressure (e.g., by pressure swing absorption (PSA)), gas purge, vacuum, lean gas sweep, or any combinations thereof. The regeneration treatment allows essentially most of the $CO_2$ that is complexed with the modified amine of the sorbent to be released. The $CO_2$ can then be stored or used in any desired manner, and the sorbent freed (regenerated) from $CO_2$ is reused in further $CO_2$ adsorption-desorption cycles.

Figure 2:
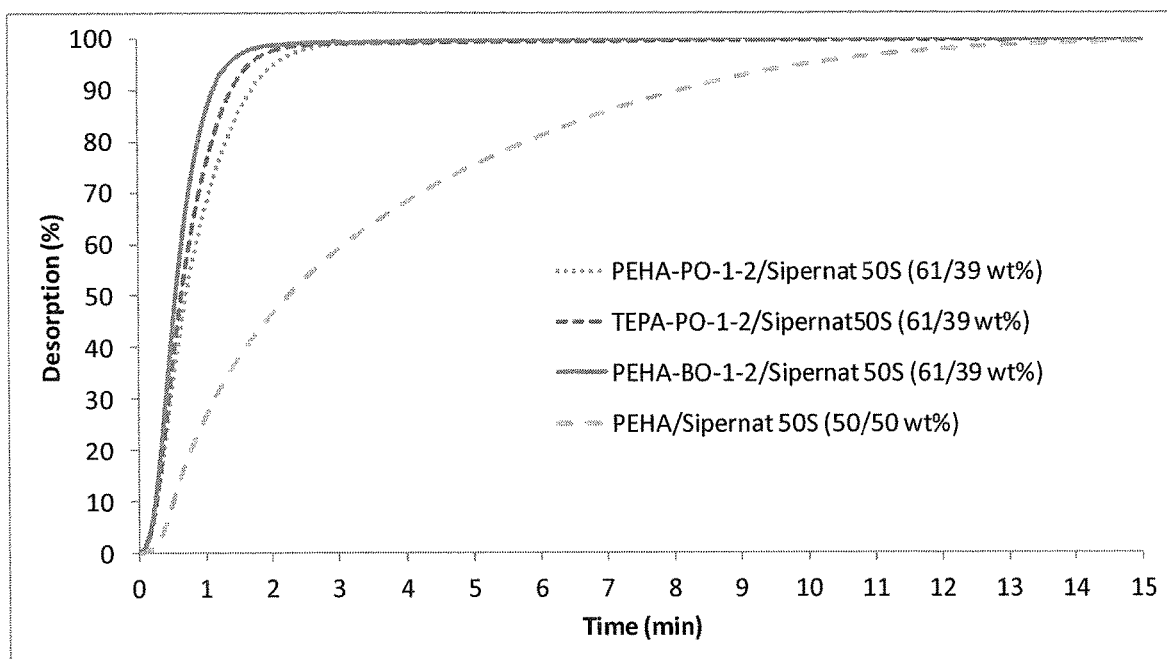
FIG. 2 illustrates: $CO_2$ desorption on unmodified and epoxy resin modified amine based solid adsorbents. TGA measurements under dry conditions. Desorption conditions: 85° C. under pure nitrogen. PO: propylene oxide; BO: 1,2-epoxybutane.

FIG. 2 and Table 1 illustrate the advantage, during the $CO_2$ desorption step, of modifying amines with epoxy resins compared to an unmodified amine. The adsorbent composed of PEHA/Sipernat 50S required more than 8 minutes to desorb 90% of the $CO_2$ at 85° C. On the other hand, the adsorbent were PEHA was modified with propylene oxide (PO) required only 1.73 min to achieve a similar desorption level and desorption was essentially over in about 3 min. The adsorbent with PEHA modified with 1,2-epoxybutane needed only 1.13 min to desorb 90% of the $CO_2$.

TABLE 1

$CO_2$ desorption characteristics of unmodified and epoxy resin modified amine based solid adsorbents. TGA measurements under dry conditions. Desorption conditions: 85° C. under pure nitrogen.

|  | time to achieve 50% desorption (min) | time to achieve 90% desorption (min) | $CO_2$ adsorption at 25° C. (mg $CO_2$/g) | $CO_2$ adsorption at 55° C. (mg $CO_2$/g) |
| --- | --- | --- | --- | --- |
| PEHA-PO-1-2/Sipernat 50S (61/39 wt %) | 0.73 | 1.73 | 117 | 144 |
| TEPA-PO-1-2/Sipernat 50S (61/39 wt %) | 0.67 | 1.43 | 94 | 135 |
| PEHA-BO-1-2/Sipernat 50S (61/39 wt %) | 0.57 | 1.13 | 109 | 122 |
| PEHA/Sipernat 50S (50/50 wt %) | 2.26 | 8.17 | 167 | 194 |

PO: Propylene oxide; BO: 1,2-epoxybutane; TGA measurements.
Adsorption under pure $CO_2$.
Desorption under pure nitrogen at 85° C.

Figure 3:
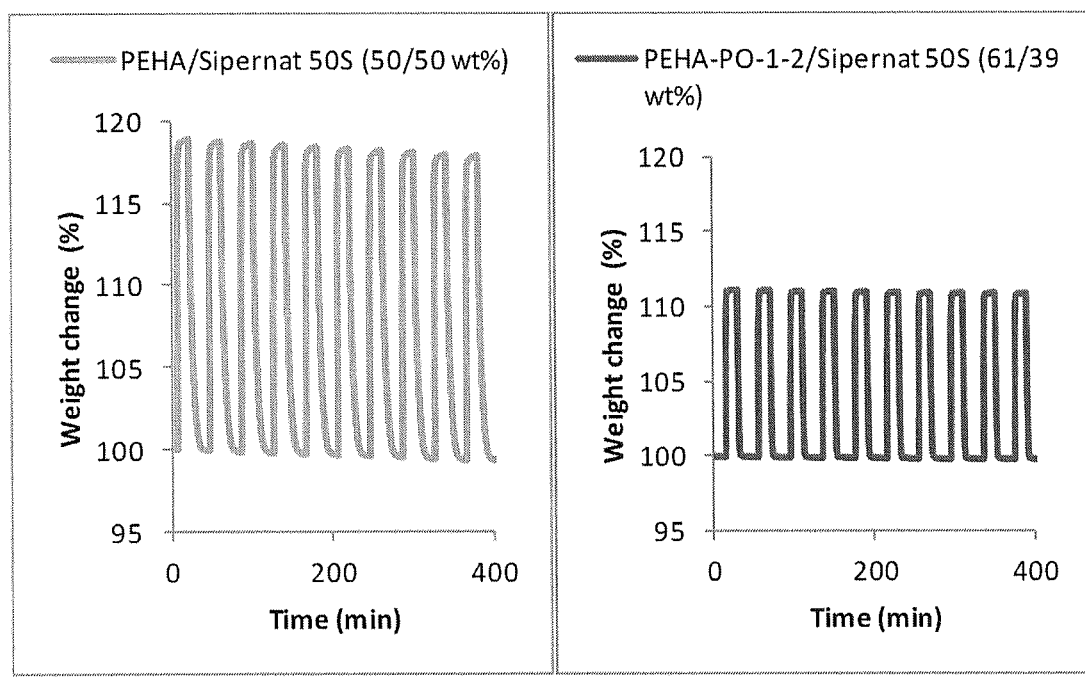
FIG. 3 illustrates $CO_2$ adsorption/desorption cycles on unmodified and propylene oxide (PO) modified pentaethylenehaxamine (PEHA) based solid adsorbents. TGA measurements under dry conditions. Adsorption and desorption under isotherm conditions at 85° C. Adsorption under pure CO2. Desorption under pure nitrogen.

FIG. 3 shows an example of higher stability obtained by the reaction of propylene oxide with pentaethylenehexamine. The adsorbent containing only PEHA on Sipernat 50S exhibited a steady decrease in weight and $CO_2$ adsorption capacity over 10 adsorption/desorption cycles in a TGA experiment under isotherm conditions. On the other hand, the adsorbent containing PEHA modified with PO on Sipernat 50S did not show a decrease in either weight or $CO_2$ adsorption capacity over the 10 adsorption/desorption cycles.

Uses and reactions of $CO_2$ include those mentioned above and as further disclosed in co-pending U.S. Pat. Nos. 7,605,293, 8,212,088 and 8,440,729, among others. The entire content of these three patents is expressly incorporated herein by reference thereto.

The sorbent according to the invention is thermally stable and does not release the supported polyamine in the temperature and/or pressure range of the adsorption operation. Further, because it is capable of regeneration and effective operation at a temperature range that can be easily maintained throughout the process, the sorbent is cost-effective for providing a high efficacy and a long life span, in addition to a high selectivity and capacity for $CO_2$ capture and separation. Because of its flexibility and versatility, the sorbent can also advantageously be used to treat large volumes of $CO_2$-containing gases from various sources.

EXAMPLES

The following examples are illustrative only and should not be interpreted as limiting the scope of the invention.

Example 1

Preparation of a Regenerable $CO_2$ Adsorbent

An adsorbent according to the invention is conveniently prepared in two steps.

Step 1: Preparation of a Modified Polyamine Species

A modified polyamine species based on pentaethylenehexamine ($H(NHCH_2CH_2)_5NH_2$, PEHA) and propylene oxide (PO) was prepared as follows. 10 g of PEHA (0.043 mol) was dissolved in 40 mL water. 5 g of PO (0.086 mol) was drawn with a syringe and then added drop-wise to the PEHA solution. The mixture was stirred for 20 hours at room temperature. After that, the temperature was progressively raised to 60° C. and kept at that temperature for 2 hours. The water was removed by rotary evaporator and followed by overnight vacuum (<1 mm Hg). The obtained product was a viscous yellow liquid. The modified polyamine is named PEHA-PO-1-2.

Step 2: Preparation of a Supported Polyamine Sorbent

A supported modified polyamine sorbent composed of 61 wt. % PEHA-PO-1-2 and 39 wt. % Sipernat 50S was prepared as follows. 3 g of PEHA-PO-1-2 was dissolved in 10 mL of water. 2 g of Sipernat 50S was suspended in 40 mL of water. PEHA-PO-1-2 solution was then slowly added to the Sipernat 50S suspension under stirring to ensure good dispersion of the modified polyamine on the support. The mixture was stirred for an additional 20 hours at room temperature. The water was then removed from the mixture by rotary evaporator and followed by overnight vacuum (<1 mm Hg). The supported polyamine adsorbent obtained was a white solid, which could be crushed and sieved to produce a solid with a uniform particle size distribution.

Example 2

Preparation of Adsorbent Based on Modified Polyamines and Precipitated Silica Sipernat 50S in "One Pot"

This example illustrates the preparation in "one pot" of a supported modified polyamine sorbent composed of 61 wt. % PEHA-PO-1-2 and 39 wt. % Sipernat 50S. 3.33 g of PEHA (0.0143 mol) was dissolved in 30 mL of water. 3.33 g of Sipernat 50S was suspended in 70 mL of water. The PEHA solution was then slowly added to the Sipernat 50S suspension under stirring to ensure good dispersion of PEHA on the support. The mixture was stirred (magnetic stirring 400 rpm) at room temperature for 2 hours. 0.0287 mol of PO (2 mL) was drawn with a syringe and then added drop-wise to the PEHA-Sipernat 50S mixture. The mixture was stirred for an additional 20 hours. After that, the temperature was progressively raised to 60° C. and kept at that temperature for 2 hours. The water was removed from the mixture by rotary evaporator and followed by overnight vacuum (<1 mm Hg). The supported polyamine adsorbent obtained was a white solid, which could be crushed and sieved to produce a solid with a uniform particle size distribution.

Example 3

Measurement of $CO_2$ Adsorption Capacity Using a PEHA-PO-1-2/Precipitated Silica (Sipernat 50S) Adsorbent Placed in a Cartridge in a Flow System. $CO_2$ Adsorption from a Mixture Containing 1000 Ppm $CO_2$ and 50% Humidity for Air Quality Purposes This example illustrates the removal of $CO_2$ from a gas mixture containing 1000 ppm $CO_2$ in air for indoor air quality purposes. The adsorbent used was PEHA-PO-1-2/precipitated silica (61/39 wt % prepared in "one pot") prepared according to example 2.

$CO_2$ adsorption data were obtained using an all-glass grease free flow system. The adsorbent was first placed in round bottom flask and evacuated (~30 mTorr) at 85° C. for 3 hours to desorb $CO_2$ and water present on the adsorbent. After this pretreatment, 1 g of the adsorbent was placed in a straight glass tube between two glass wool plugs thermostated at 25° C. The adsorbent weight (1 g) after pretreatment was used for the later calculation of the $CO_2$ adsorption capacities. For the adsorption measurements a Horiba VIA-510 $CO_2$ analyzer equipped with an IR detector specifically intended for $CO_2$ measurements was placed in-line with the adsorption setup. Before the experiment, the analyzer was calibrated with reference gases; $CO_2$ in air and ultra zero grade air for the zero. An air mixture containing 1000 ppm $CO_2$ and 50% moisture (dew point of 14° C.) was used for the adsorption measurements. The air flow (~335 mL/min) was then opened on the adsorbent bed. Almost immediately the $CO_2$ concentration in the gas outlet fell to a value lower than 10 ppm, signaling essentially complete $CO_2$ adsorption from the air. The $CO_2$ concentration was recorded as a function of time via LabView 8.6. After an initial period close to 0 ppm $CO_2$, the concentration in the outlet gas started to increase. After saturation of the adsorbent, when the $CO_2$ concentration reached a value close to the inlet value (1000 ppm), the gas flow was stopped. The total adsorption capacity was determined to be 106 mg $CO_2$/g adsorbent (2.4 mmol $CO_2$/g adsorbent) after 5 hours of adsorption.

The desorption of the $CO_2$ on the adsorbent was performed by heating the adsorbent containing glass tube to 50° C. with a heating tape and then passing a flow of air containing 400 ppm $CO_2$ and 13% humidity (dew point of 14° C.) (335 ml/min) through it for 1 hour. The $CO_2$ concentration was recorded as a function of time via LabView 8.6. Heating resulted in an increase of the $CO_2$ concentration to values above 5000 ppm followed by a decrease until a $CO_2$ concentration close to the inlet concentration (400 ppm $CO_2$) was reached.

Figure 4:
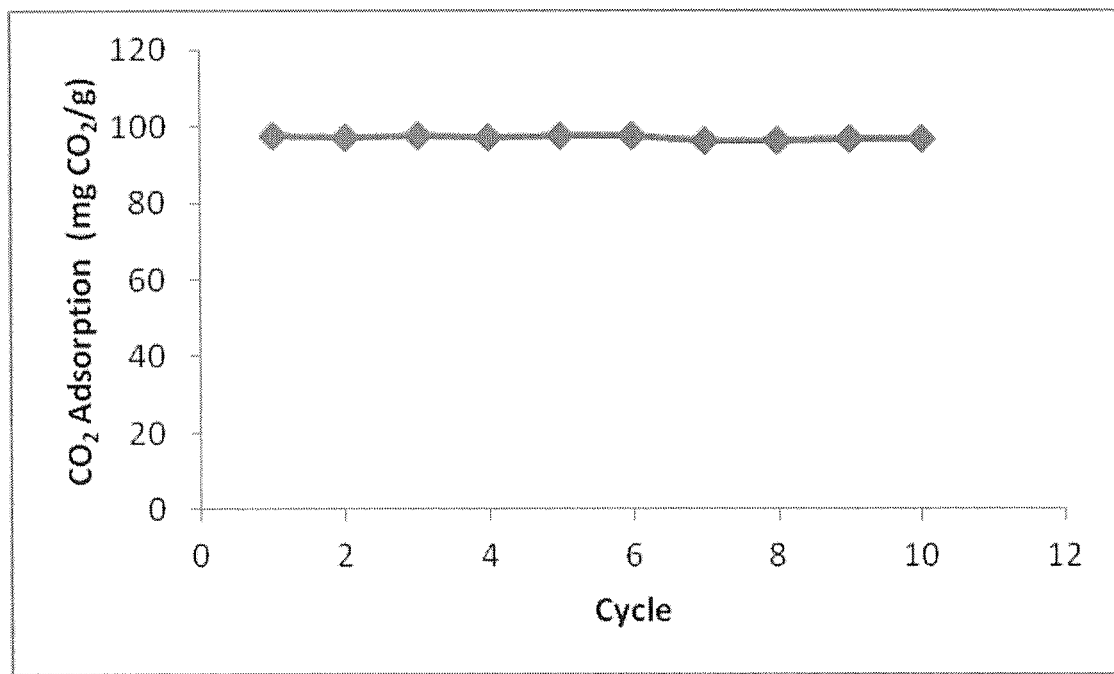
FIG. 4 illustrates $CO_2$ adsorption capacity over 10 adsorption/desorption cycles on PEHA-PO-1-2/precipitated silica (61/39 wt % prepared in "one pot"). Adsorption at 1000 ppm $CO_2$ in air at 25° C. Desorption at 400 ppm $CO_2$ in air at 50° C. Under humid conditions.
Figure 5:
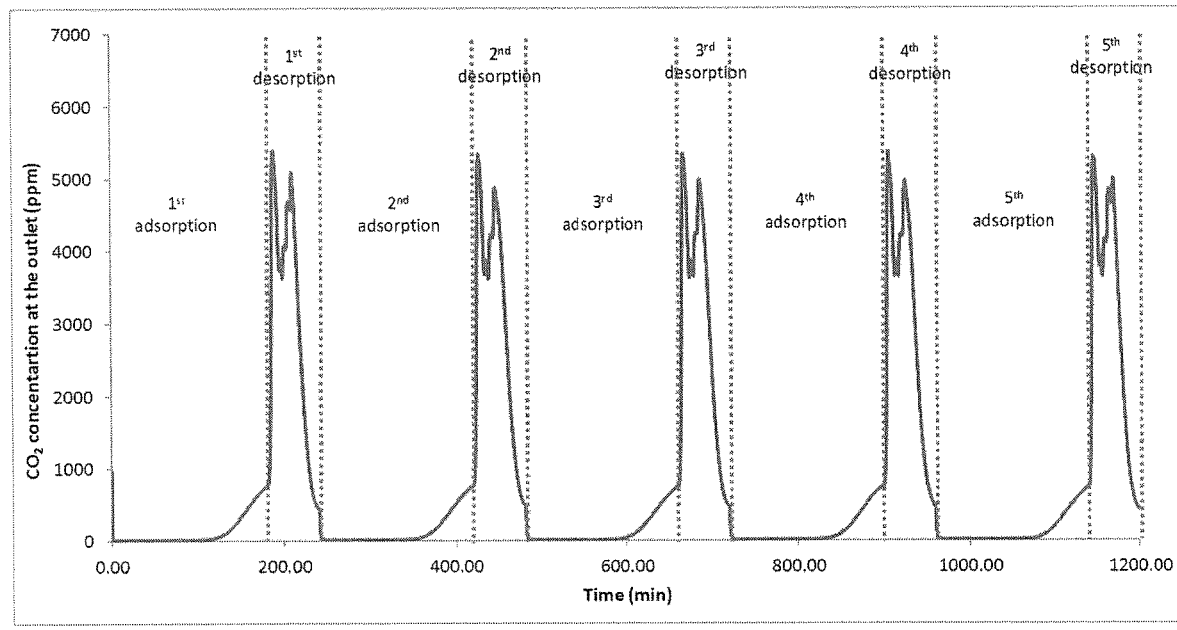
FIG. 5 illustrates $CO_2$ concentration at the outlet of the adsorbent bed over the first 5 adsorption/desorption cycles on PEHA-PO-1-2/precipitated silica (61/39 wt % prepared in "one pot"). Adsorption at 1000 ppm $CO_2$ in air at 25° C. Desorption at 400 ppm $CO_2$ in air at 50° C. Under humid condition.

This initial adsorption/desorption cycles was followed by 10 additional adsorption/desorption cycles under the same conditions except for the adsorption time which was reduced to 3 h (adsorption at 25° C. for 3 h, 1000 ppm $CO_2$ in air, 50% humidity (dew point of 14° C.), 335 mL/min and desorption at 50° C. for 1 h, 400 ppm $CO_2$ in air, 13% humidity (dew point of 14° C.), 335 mL/min). The adsorption capacity remained stable at around 96-98 mg $CO_2$/g adsorbent as can be seen in FIG. 4. The $CO_2$ concentration profile during the adsorption/desorption cycles was very similar from cycle to cycle as observed in FIG. 5 showing the $CO_2$ concentration as measured at the outlet of the adsorbent bed.

Example 4

Measurement of $CO_2$ Adsorption Capacity Using a TEPA-PO-1-2/Precipitated Silica Adsorbent Placed in a Cartridge in a Flow System. $CO_2$ Adsorption from a Mixture Containing 1000 Ppm $CO_2$ and 50% Humidity for Air Quality Purposes This example illustrates the removal of $CO_2$ from a gas mixture containing 1000 ppm $CO_2$ in air for indoor air quality purposes. The adsorbent used was TEPA-PO-1-2/precipitated silica (61/39 wt % prepared in "one pot").

Figure 6:
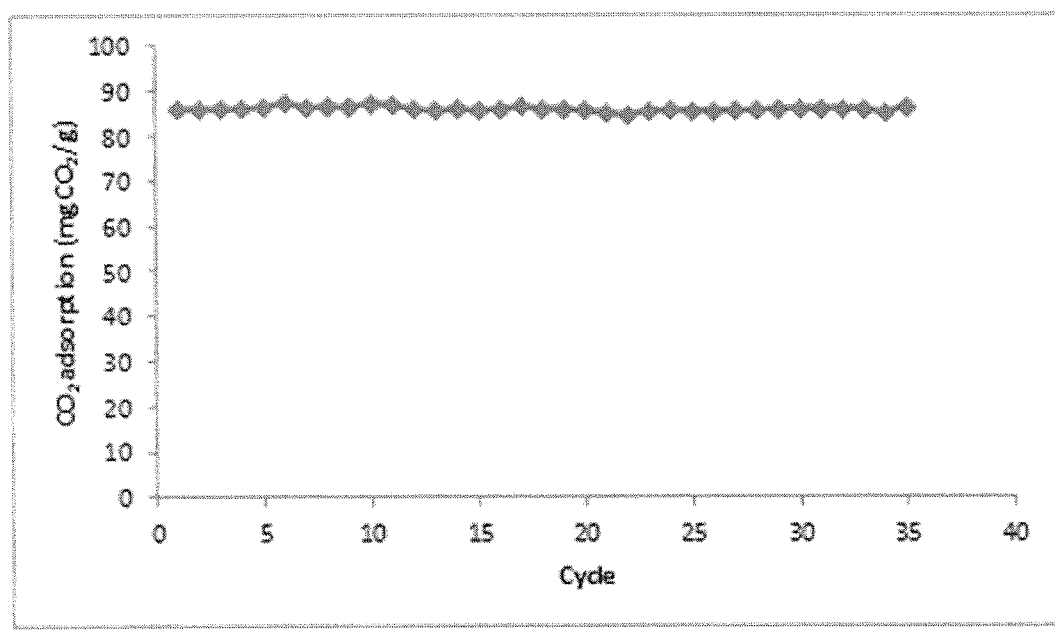
FIG. 6 illustrates $CO_2$ adsorption capacity over 35 adsorption/desorption cycles on TEPA-PO-1-2/precipitated silica (61/39 wt % prepared in "one pot"). Adsorption at 1000 ppm $CO_2$ in air at 25° C. Desorption at 400 ppm $CO_2$ in air at 50° C. Under humid conditions.

The same procedure as described in example 3 was used. Over 35 cycles of adsorption/desorption the adsorption capacity remained stable at around 84-87 mg $CO_2$/g adsorbent as can be seen in FIG. 6.

What is claimed is:

1. A solid carbon dioxide sorbent with structural integrity for adsorbing carbon dioxide from a gas mixture, comprising a modified polyamine which is supported upon and within a solid support, wherein the modified polyamine is a reaction product of an excess of an amine selected from the group consisting of tetraethylenepentamine, pentaethylenehexamine, hexaethyleneheptamine, triethylenetetramine, diethylenetriamine, polyethylenimine and a mixture thereof, and a monoepoxide selected from the group consisting of ethylene oxide, propylene oxide, 1,2-epoxybutane, 1,2-epoxypentane and 1,2-epoxyhexane to provide a material with amine functionalities, wherein the solid support is (a) a nano-structured support of silica, silica-alumina, alumina, titanium oxide, calcium silicate, carbon nanotubes, carbon, or a mixture thereof and having a primary particle size of less than about 100 nm; or (b) a natural or synthetic clay or a mixture thereof.

2. The carbon dioxide sorbent according to claim 1, which has a high surface area for solid-gas contact, wherein the carbon dioxide sorbent is regenerative for capturing and separating carbon dioxide for at least one cycle at temperatures of 85° C. or less from a gas containing carbon dioxide.

3. The carbon dioxide sorbent according to claim 1, which has a high surface area for solid-gas contact, wherein the carbon dioxide sorbent is regenerative for capturing and separating carbon dioxide for at least one cycle at temperatures of 55° C. or less from a gas containing carbon dioxide.

4. A solid carbon dioxide sorbent with structural integrity for adsorbing carbon dioxide from a gas mixture, comprising a modified polyamine which is supported upon and within a solid support, wherein the modified polyamine is a reaction product of an excess of an pentaethylenehexamine and propylene oxide to provide a material with amine functionalities, wherein the solid support is (a) a nano-structured support of silica, silica-alumina, alumina, titanium oxide, calcium silicate, carbon nanotubes, carbon, or a mixture thereof and having a primary particle size of less than about 100 nm; or (b) a natural or synthetic clay or a mixture thereof.

5. The carbon dioxide sorbent according to claim 1, wherein the solid support has a primary particle size of between 3 and 50 nm.

6. The carbon dioxide sorbent according to claim 1, wherein the solid support has a primary particle size of between 3 and 30 nm.

7. The carbon dioxide sorbent according to claim 1, wherein the solid support has a primary particle size of between 3 and 15 nm.

8. The carbon dioxide sorbent according to claim 1, wherein the modified polyamine is present in an amount of 1% to 70% by weight of the sorbent, or in an approximately equal amount by weight as the support.

9. The carbon dioxide sorbent according to claim 1, wherein the modified polyamine is present in an amount of 1% to 40% by weight of the sorbent, or in an approximately equal amount by weight as the support.

10. The carbon dioxide sorbent according to claim 1, wherein the natural or synthetic clay or a mixture thereof comprises montmorillonite.

11. The carbon dioxide sorbent according to claim 1, which has a high surface area for solid-gas contact, wherein the carbon dioxide sorbent is regenerative for capturing and separating carbon dioxide for at least one cycle at temperatures of 55° C. or less from air or a gas mixture containing carbon dioxide in a concentration below 1 percent by volume.

12. The carbon dioxide sorbent according to claim 1, which has a high surface area for solid-gas contact, wherein the carbon dioxide sorbent is regenerative for capturing and separating carbon dioxide for at least one cycle at temperatures of 55° C. or less from ambient air with carbon dioxide concentrations between 200 ppm and 5000 ppm by volume.

13. The carbon dioxide sorbent according to claim 1, in which the modified polyamine is present in an amount of 1% to 90% by weight of the sorbent, or in an approximately equal amount by weight as the support.

14. The carbon dioxide sorbent according to claim 1, which further comprises a polyethylene oxide or a polyol or various mixtures thereof in an amount of 1 up to about 25% by weight of the sorbent, wherein the polyol is glycerol, oligomers of ethylene glycol or polyethylene glycol, and the polyethylene oxides may be present as their corresponding ethers.

15. The carbon dioxide sorbent according to claim 1 in which the modified polyamine is bound to the surface of the support by grafting methods with various species.

* * * * *